United States Patent [19]
Moreau et al.

[11] 3,933,944
[45] Jan. 20, 1976

[54] α,α'-BIS(PHOSPHONO)DICARBOXYLIC ACID DERIVATIVES

[75] Inventors: Jerry P. Moreau; Leon H. Chance; Gordon J. Boudreaux, all of New Orleans; George L. Drake, Jr., Metairie, all of La.

[73] Assignee: The United States of America as represented by the Secretary of Agriculture, Washington, D.C.

[22] Filed: Dec. 4, 1972

[21] Appl. No.: 311,609

[52] U.S. Cl. .............. 260/932; 260/969; 427/394; 428/921
[51] Int. Cl.² .......................................... C07F 9/40
[58] Field of Search ................................. 260/932

[56] References Cited
OTHER PUBLICATIONS

Moreau et al., "Jou. of Chem. and Eng. Data," Vol. 17, No. 2, April 1972, pp. 252–254.

*Primary Examiner*—Anton H. Sutto
*Attorney, Agent, or Firm*—M. Howard Silverstein; Max D. Hensley

[57] ABSTRACT

Derivatives of dicarboxylic acids containing a phosphono group in the alpha and alpha prime position have been made. These have a wide variety of uses as intermediates. Specifically, one of the new compounds is useful in imparting wrinkle resistance as well as flame retardance to cellulosic textiles.

3 Claims, No Drawings

α,α-BIS-(PHOSPHONO)DICARBOXYLIC ACID DERIVATIVES

A non-exclusive, irrevocable, royalty-free license in the invention herein described, throughout the world for all purposes of the United States Government, with the power to grant sublicenses for such purposes, is hereby granted to the Government of the United States of America.

This invention relates to dicarboxylic acid derivatives which contain a phosphono group in the $\alpha$ and $\alpha'$ positions. More specifically, this invention relates to the preparation of $\alpha,\alpha'$-bis phosphono dicarboxylic acid derivatives with more than four carbon atoms in the dicarboxylic acid chain. These have never been prepared by the Michaelis-Arbuzov reaction of the $\alpha,\alpha'$-dibromo dicarboxylic acid or its derivatives. These compounds have a wide variety of uses, of which of special interest is in textile applications wherein these serve as intermediates. Of the new compounds, the methylol derivatives of $\alpha,\alpha'$-bis(diethylphosphono)adipamide is specifically useful for imparting wrinkle resistance and flame retardance to cellulosic fabrics when used alone or in combination with a resin.

The primary object of this invention is to disclose the preparation of new dicarboxylic acid derivatives containing a phosphono group in the $\alpha$ and $\alpha'$ positions.

A second object of this invention is to provide a method of preparing these new compounds so that they may be made available to the areas of textile finishing, synthetic fibers, lubricants, and surface active agents.

Another object of this invention is to make this method of preparing these new derivatives available so that these compounds may be prepared and used as intermediates in the preparation of other new and useful compounds and polymers.

The novelty of the invention lies in the fact that $\alpha,\alpha'$-bis phosphono dicarboxylic acid derivatives have never been prepared in which there are more than four carbon atoms in the dicarboxylic acid chain; and also by the fact that they have never been prepared by the Michaelis-Arbuzov reaction of the $\alpha,\alpha'$ dibromo dicarboxylic acid or its derivative. As a consequence of the preparation of these new compounds, they may be used in themselves or as intermediates in the preparation of other compounds and polymers which may in turn be used in many areas such as textile finishing, lubrication, surface activity, and synthetic fibers.

Compounds of this invention comprise $\alpha,\alpha'$-bis phosphono dicarboxylic acid derivatives of the general formula:

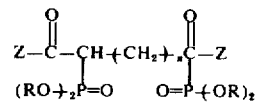

I where
$n = 0$ to $30$
$Z = OR, NH_2, NH-R', NR'_2$
$R = R', H, Na, K, NH_4, R'NH_3$
$R' =$ alkyl radical, haloalkyl radical, aryl radical, or hydroxy alkyl radical Some examples of the reactions used to prepare specific compounds of the general formula I, are shown in the following equations:

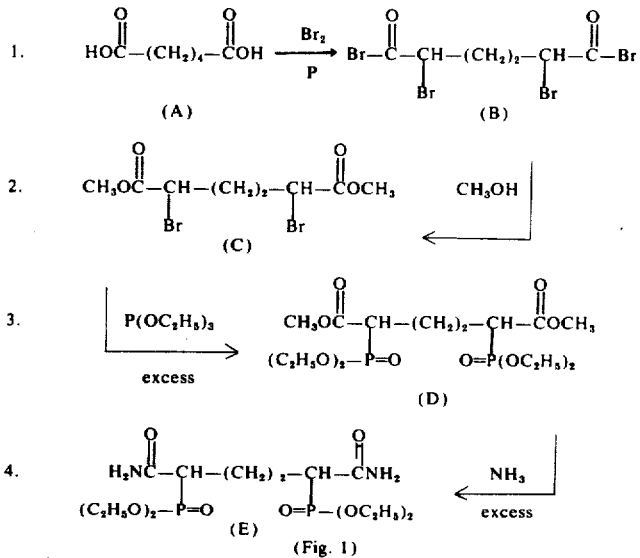

(Fig. 1)
Note: Products (D), (E), and (J) are Compounds of this invention.

A dicarboxylic acid such as adipic acid (A), may be reacted with bromine and red phosphorus by the Hell-Volhard-Zelinskii reaction to produce the $\alpha,\alpha'$ dibromo diacylbromide (B). (B) may then be reacted with methanol to give dimethyl $\alpha,\alpha'$-dibromoadipate (C). The $\alpha,\alpha'$-bis phosphono ester (D) may be prepared by the Michaelis-Arbuzov reaction by reacting (C) with triethyl phosphite. Finally, (D) may be reacted with ammonia in aqueous solution to give the $\alpha,\alpha'$-bis phosphono adipamide (E).

Other chemicals and reactions may be used in order to obtain the same or similar compounds shown in FIG. 1. In equation (1), any other known method may be used for brominating in the $\alpha,\alpha'$- positions. For example, thionyl chloride and bromine may be used to give the $\alpha,\alpha'$ bromo diacylchloride, which in turn may be used to obtain compound (C).

In equation (2), various alcohols may be used such as ethyl, propyl, isoproyl, amyl, etc. to give different $\alpha,\alpha'$ dibromo dicarboxylic esters before proceeding to equation (3). Water may also be used to give the $\alpha,\alpha'$ dibromo dicarboxylic acid.

Before proceeding to equation (3), the bromine atoms in the $\alpha,\alpha'$ positions may be replaced with iodine in order that subsequent substitution or reaction in the $\alpha,\alpha'$ positions will be easier.

Reaction (3) may also be accomplished by the Michaelis-Becker reaction using the metal salt, such as sodium or potassium, of a dialkyl phosphite.

Reaction (4) may be performed using aqueous ammonia, alcholic ammonia, or liquid ammonia with and without pressure.

Compounds containing the phosphono group in the $\alpha,\alpha'$ positions such as (D) may be used as intermediates in the preparation of other useful compounds as shown by the following reactions:

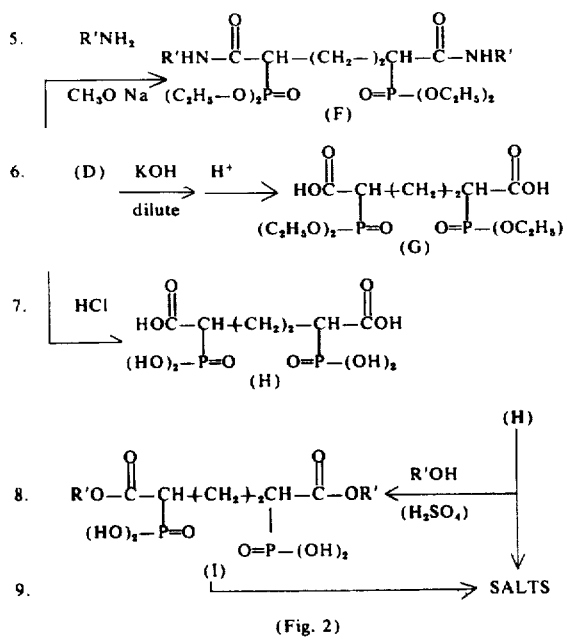

(Fig. 2)

The carboxyl ester groups of (D) may be reacted with primary aliphatic and aromatic amines in the presence of a molar equivalent of sodium methoxide to give the respective secondary amides as shown in equation (5). The carboxyl ester groups of (D) may be hydroyzed with dilute alcoholic KOH as shown in equation (6). The alkali salt is then reacted with an acid such as HCl, with little effect on the phosphono ester groups, to give compound (G).

On the other hand, as shown in equation (7), all ester groups may be hydrolyzed with 20-35% aqueous HCl to give compound (H).

Compound (H) may then be reacted with an appropriate alcohol, using $H_2SO_4$ as a catalyst, to esterify the carboxyl acid groups and give compound (I).

Compound (H) may also be hydrolyzed with dilute alcoholic NaOH at pH of approximately 5.0, where the first acidic hydrogen of the phosphono groups are replaced with Na to give the di Na salt of (H); and at pH of approximately 8.0 where the carboxylic hydrogens are replaced with Na to give the tetra Na salt of (H); and at pH of approximately 11 where the hexa Na salt of (H) is formed.

Compound (I) may also be hydrolyzed with dilute alcoholic NaOH (at pH of approximately 6.5) to give di- and (at pH of approximately 10) to give tetra- phosphono salts of dicarboxylic acid esters. Other than alkali metal salts, salts of ammonia, amines, and alkanolamines may also be prepared.

Other useful reactions involving compounds such as $\alpha,\alpha'$-bis(diethylphosphono)adipamide, (E), are shown in FIG. 3.

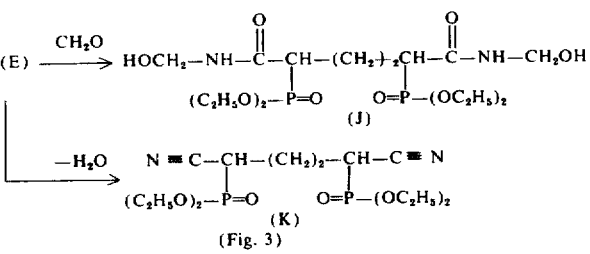

(Fig. 3)

Equation 10 shows the reaction of compound (E) with formaldehyde to give the dimethylol compound (J). Possibly more formaldehyde could be used to give the tetramethylol derivative as well.

Primary amide groups such as those present in compound (E) could also be subjected to a dehydration reaction, as shown by equation (II), to give the dinitrile (K).

UTILITY OF COMPOUNDS OF THE PRESENT INVENTION

Compounds of the type shown in FIGS. 1, 2, and 3 have wide utility in many fields of interest. Firstly, compounds of this type can be used as intermediates in the preparation of many other new and unusual useful compounds and polymers.

Salts as prepared in equation (9) would have wetting, foaming, detergent and other surface active properties.

Esters such as those prepared in equation (3) could be used as plasticizers and lubricants particularly if a long chain dicarboxylic acid derivative were used.

All of the compounds containing a phosphono group in the $\alpha,\alpha'$ positions of the dicarboxylic acid derivative may be useful insecticides and have physiological activity as well.

The formaldehyde derivatives as prepared in equation (10) — a process of the present invention — would be useful in the chemical finishing of cellulosic materials and textiles, such as cotton and rayon, to impart such properties as crosslinking, rot resistance, and flame retardancy. Compounds such as (J) can be used by themselves or copolymerized with other methylol derivatives to impart desirable properties to textiles and cellulosic materials.

Another important use of $\alpha,\alpha'$-bis phosphono derivatives of dicarboxylic acids is in the preparation of polymers for use in the production of synthetic fibers as shown in equations (12) and (13).

12. (G) + H$_2$N—R'—NH$_2$ ⟶

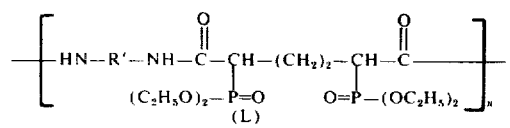

(L)

13. (G) + HO—R'—OH ⟶

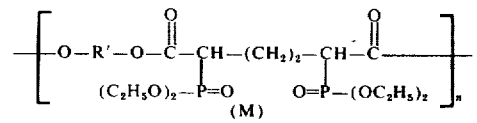

(M)

Compounds such as α,α'-bis(diethylphosphono)adipic acid, (G), may be used in place of adipic acid to react with amines in the preparation of polyamide fibers. Compounds such as (G) may also be reacted with glycols to produce polyester fibers. Polymers such as (L) and (M) may be used to produce synthetic fibers having flame retardant properties because of the presence of phosphorus atoms in the polymer backbone.

Polyesters such as (M) would also be more hydrolytically stable since a carboxylate group containing a phosphono group in the α position is known to be much more stable toward hydrolysis than an ester which is unsubstituted in the α position. This is the reason why polyesters prepared from terephthalic acid are preferred over polyesters prepared from adipic acid.

Another important feature of the α,α'-bis phosphono dicarboxylic acid derivatives of this invention is the presence of stereoisomers, which is of practical as well as theoretical interest. Compounds such as (D) and (E) contain two assymetrical carbon atoms in the same molecule and therefore in their preparation may be obtained in many different isomeric forms or as a mixture of stereoisomers. Possibly they could be prepared and isolated as optically active compounds and/or used in the preparation of other optically active compounds. These compounds would be of practical value since certain optically active compounds are effective as bactericides whereas their isomers are not effective.

The possible existence of stereoisomers of α,α'-bis phosphono dicarboxylic acid derivatives stems from the fact that stereoisomers are obtained in the preparation of compound (C), a known compound. Compound (C) has been isolated as the meso- form, as the d,l-racemate and as a mixture of meso- form and the d,l-racemate. Therefore, these isomers could be isolated and purified before proceeding to the preparation of the α,α'-bis phosphono derivative such as shown in equations (3) and (4).

The compounds of this invention and the methods of preparation are beyond the scope of the prior art in that the only α,α'-bis phosphono derivatives of a dicarboxylic acid ever reported are those for succinic acid, in which case acetylenedicarboxylic acid was used as the starting material. In this prior method, a dialkyl or trialkyl phosphite was added to the triple bond of the C$_4$ dicarboxylic acid, or its derivative, to give the respective α,α'-bis phosphono compounds. However, such a method would be impractical if not impossible with dicarboxylic acids (or their derivatives) containing more than four carbon atoms in the chain. Also, the α,α'-bis phosphono derivatives of the C$_4$ dicarboxylic acid were prepared by addition of the phosphono groups across a triple bond and not by the Michaelis-Arbuzov reaction of the α,α'-dibromo dicarboxylic acid derivative as in this invention.

The following examples illustrate procedures that have been successfully used in the application of this invention and are not meant as a limitation thereof.

EXAMPLE 1

Preparation of Dimethyl α,α'-bis(Diethylphosphono) adipate (D).

The isomeric meso- form of dimethyl α,α'-dibromoadipate (C) (100 grams, 0.3 mole) and triethyl phosphite (150 grams, 0.9 mole) were heated at 150°–180°C. Nitrogen was swept through the system to facilatate the removal of ethyl bromide. The reaction mixture was heated for three hours, after which the evolution of ethyl bromide ceased. This occurred after collecting ca. 90% of the theoretical amount of ethyl bromide.

The reaction mixture was fractionally distilled to give (D) (90 grams, 0.2 mole); b.p. 192°C (0.09 mm); $n_D^{20}$ 1.4572. Additional (D) can be obtained from the adjacent fractions to give a total yield of 75–80%. (D) solidified to a waxy white solid.

The NMR spectrum in CDCl$_3$ showed a triplet centered at δ = 1.35, (C$\underline{H}_3$CH$_2$O)$_2$; a complex multiplet centered at δ = 2.00 -(CH$_2$)-; two complex multiplet centered at δ = 3.00, -CH(P)-; a singlet at δ = 3.80, CH$_3$O-; and a complex multiplet centered at δ 4.20, (CH$_3$C$\underline{H}_2$O)$_2$, with ratios of 6:2:1:3:4.

The IR spectrum as a smear on a KBr plate showed absprption bands at 1740 cm$^{-1}$, (C=O) ester; 1250 cm$^{-1}$, P=O; 1160 cm$^{-1}$, P-OEt; and 1020 cm$^{-1}$, P-O-C.

Anal. Calcd. for C$_{16}$H$_{32}$O$_{10}$P$_2$: C, 43.05; H, 7.23; P, 13.88; M.W., 446. Found: C, 43.01; H, 7.14; P, 14.00, M.W., 436 (benzene).

EXAMPLE 2

Preparation of α,α'-bis(Diethylphosphono) adipamide (E).

D, from Example 1 (45 grams, 0.1 mole) was dissolved in absolute methanol (30 grams) and conc. ammonium hydroxide (170 grams, 29% NH$_3$) was added. The solution was cooled to 5 C while saturating with ammonia gas, then allowed to stand at room temperature for two weeks. The white crystalline solid, which began to precipitate after the second day, was filtered and washed with cold water and then with acetone to give a 55% yield of (E) (23 grams, 0.055 mole); m.p. 232°–4°C. From a smaller run, a 44% yield of (E) was obtained with m.p. 235°–235.5°C.

The NMR spectrum in DMSO-d$_6$ showed a triplet centered at δ =1.23, C$\underline{H}_3$CH$_2$O)$_2$; a complex multiplex centered at δ -1.67,-(-CH$_2$)-; a complex multiplet centered at δ =3.17,-(-CH(P)-; a complex multiplet centered at δ -4.06, CH$_3$C$\underline{H}_2$O)$_2$; and two signals at δ =7.17 and 7.50, coalesing at 80°C, attributed to hindered rotation of $\underline{H}_2$N-, with ratios of 6:2:1:4:2.

The IR spectrum in KBr disc showed absorption bands at 3280 cm$^{-1}$ and 3120 cm$^{-1}$, NH$_2$ stretching; 1680 cm$^{-1}$, (C=O) amide I; 1630 cm$^{-1}$, amide II; 1230 cm$^{-1}$, P=O; 1160 cm$^{-1}$, P-O-Et; and 1020 cm$^{-1}$, P-O-C.

Anal. Calcd. for C$_{14}$H$_{30}$N$_2$O$_8$P$_2$: C, 40.39; H, 7.26 N, 6.73; P, 14.88 Found: C, 40.37, H, 7.34; N, 6.70, P, 14.96.

EXAMPLE 3

Reaction of (E) with formaldehyde yields bis(N,N'-hydroxymethyl)α,α'-bis(diethylphosphono)Adipamide (J) -E, from Example 2 (2.08 grams, 0.005 mole), was slowly added to 37% formaldehyde (1.00 grams, 0.01 mole) at approximately 75°C while trying to maintain pH above 7 with 3% Na$_2$CO$_3$. It took approximately 45 minutes to add compound E and Na$_2$CO$_3$ and get everything in solution. The solution was then heated an additional one and one-half hours above 50°C then the solution was concentrated under vacuum below 50°C to give a clear glass-like solid. The solid was dispersed in hot acetone, cooled and the liquid decanted from a semi-solid white residue. The white residue was shaken in a mixture of acetone and benzene then finally shaken three times with benzene alone. Solvent was removed under vacuum to give a white fluffy solid residue (1.07 gms) which was hygroscopic and had a m.p. of approximately 150°C. Analyses on the material was 5.65% N and 13.28% P. Theoretical analyses for compound (J) is 5.88% N and 13.00% P.

EXAMPLE 4

Application of a methylol derivative of (E) to Cotton.

A methylol derivative of compound (E) was prepared in a similar manner as described in Example 3 except 5 moles of formaldehyde was used for each mole of compound (E). This methylol derivative was not isolated but simply diluted with water to give a solution containing 20% solids calculated as the concentration of compound (E) used. Approximately 2% Zn(NO$_3$)$_2$.6H$_2$O was added as a catalyst. This solution was used to treat a sample of 100% cotton printcloth by a paddry-care technique. The treated printcloth had a dry weight add-on of approximately 11% and showed flame retardant properties as measured by a 90° match test angle. [Reeves, W.A., et al., Text. Res. J. 23, 529 (1953)] The sample also showed wash-wear properties as measured by a conditioned wrinkle recovery angle (ASTM Method D 1295-60T) of 251° as compared to the control which was only 179°.

EXAMPLE 5

Application of Methylol derivative of (E) to cotton and inclusion of a resin.

A methylol derivative of compound (E) was prepared in a similar manner as described in Example 3 except a slight excess of 2 moles of formaldehyde was used for each mole of compound (E). This methylol derivative was not isolated but was diluted with water. Trimethylol melamine (TMM) resin and Zn(NO$_3$)$_2$·6-H$_2$O was then added to this solution. This solution was diluted to give a final solution containing 20% compound (E), 7.5% TMM and 2% catalyst.

This solution was used to treat a sample of 100% cotton sateen by a pad-dry-cure technique. The treated sample had a final weight add-on of 16.3% and had flame retardant properties as measured by a match test angle of 105°. The same sample also had good wash-wear properties as measured by a 272° conditioned wrinkle recovery angle as compared to the control which measured 192°.

Similar experiments were conducted as described above but using various commercial resins such as: Aerotex 23 special, Valmet HM, Resloom HP, Aerotex P225 etc.

The properties of flame retardancy and wrinkle recovery were also varied by changing the weight ratio of the methylol derivative of compound (E) used with respect to the weight of resin used.

We claim:
1. Dimethyl α,α'-bis(diethylphosphono)adipate.
2. α,α'-Bis(diethylphosphono)adipamide.
3. Bis(N,N'-hydroxymethyl)α,α'-bis(diethylphosphono)adipamide.

* * * * *